(12) United States Patent
Georgeson et al.

(10) Patent No.: US 7,240,556 B2
(45) Date of Patent: Jul. 10, 2007

(54) ANGLE BEAM SHEAR WAVE THROUGH-TRANSMISSION ULTRASONIC TESTING APPARATUS AND METHOD

(75) Inventors: Gary E. Georgeson, Federal Way, WA (US); Michael D. Fogarty, Auburn, WA (US)

(73) Assignee: The Boeing Company, Chicago, IL (US)

( * ) Notice: Subject to any disclaimer, the term of this patent is extended or adjusted under 35 U.S.C. 154(b) by 140 days.

(21) Appl. No.: 11/079,425

(22) Filed: Mar. 14, 2005

(65) Prior Publication Data

US 2006/0201252 A1   Sep. 14, 2006

(51) Int. Cl.
*G01N 29/24* (2006.01)

(52) U.S. Cl. ............... 73/641; 73/620; 73/634; 73/644

(58) Field of Classification Search ............ 73/641, 73/599, 600, 602, 643, 644, 634, 635, 620
See application file for complete search history.

(56) References Cited

U.S. PATENT DOCUMENTS

| | | | |
|---|---|---|---|
| 4,807,476 A | 2/1989 | Cook et al. | |
| 5,586,085 A * | 12/1996 | Lichte | 367/99 |
| 6,250,159 B1 * | 6/2001 | Kreier et al. | 73/602 |
| 6,484,583 B1 | 11/2002 | Chennell et al. | |
| 6,658,939 B2 | 12/2003 | Georgeson et al. | |
| 6,722,202 B1 * | 4/2004 | Kennedy et al. | 73/634 |
| 2002/0017140 A1 | 2/2002 | Georgeson et al. | |
| 2003/0154801 A1 | 8/2003 | Georgeson | |
| 2004/0103721 A1 | 6/2004 | Georgeson | |
| 2004/0123674 A1 * | 7/2004 | Moscaritolo et al. | 73/861.27 |
| 2006/0053891 A1 * | 3/2006 | Georgeson et al. | 73/624 |
| 2006/0053892 A1 * | 3/2006 | Georgeson et al. | 73/634 |
| 2006/0162456 A1 * | 7/2006 | Kennedy et al. | 73/620 |

OTHER PUBLICATIONS

Panametrics-NDT Ultrasonic Transducer Technical Notes; http://www.panametrics-ndt.com/ndt/ndt_transducers/downloads/transducer_technotes.pdf (Dec. 22,2004).
Panametrics-NDT Ultrasonic Transducer Catalog; http://www.panametrics-ndt.com/ndt/ndt_transducers/downloads/transducer_catalog.pdf (Dec. 22,2004).

(Continued)

*Primary Examiner*—Hezron Williams
*Assistant Examiner*—Jacques M Saint Surin
(74) *Attorney, Agent, or Firm*—Alston & Bird LLP (57) ABSTRACT

Improved methods, systems, and apparatus for inspecting a structure using angle beam shear wave through-transmission ultrasonic signals involves positioning transducers at offset positions on opposing sides of the structure and permits inspection of the inside of the structure beneath surface defects and features. Magnetic coupling can be used for supporting a pair of leader-follower probes and defining offset positions between angle beam shear wave transducers carried by the probes. Inspection data can be collected for supporting real-time generation of three-dimensional image representations of the structure and of internal defects and features of the structure. Image generation and resolution using inspection data from angle beam shear wave ultrasonic signals can be supplemented using pulse-echo ultrasonic inspection data.

34 Claims, 3 Drawing Sheets

OTHER PUBLICATIONS

Angle Beam Ultrasonic Transducers & Wedges; http://www.panametrics-ndt.com/ndt/ndt_transducers/angle_beam_wedge/index.html (Dec. 22, 2004) 2 pages.

Standard Angle Beam Ultrasonic Transducers & Wedges; http://www.panametrics-ndt.com/ndt/ndt_transducers/angle_beam_wedge/standard.html (Dec. 22, 2004) 3 pages.

Miniature Screw-in Ultrasonic Transducer; http://www.panametrics-ndt.com/ndt/ndt_transducers/angle_beam_wedge/mini_screwin.html (Dec. 22, 2004) 3 pages.

Miniature Screw-in Ultrasonic Transducer; http://www.panametrics-ndt.com/ndt/ndt_transducers/angle_beam_wedge/mini_snapin.html (Dec. 22, 2004) 3 pages.

AWS Snail, AWS Accupath & O.P.Angle Beam; http://www.panametrics-ndt.com/ndt/ndt_transducers/angle_beam_wedge/aws_snail_accupath.html (Dec. 22, 2004) 3 pages.

Integral, Shear Wave & Contoured Ultrasonic Transducers; http://www.panametrics-ndt.com/ndt/ndt_transducers/angle_beam_wedge/integral_angle_wedge.html (Dec. 22, 2004) 3 pages.

Integral Angle Beam Ultrasonic Probes for Shear Wave Propagation; http://www.panametrics-ndt.com/ndt/ndt_transducers/angle_beam_wedge/integral_angle_probes.html (Dec. 22, 2004) 2 pages.

CentraScan Series Composite Element Ultrasonic Transducer; http://www.panametrics-ndt.com/ndt/ndt_transducers/composite.html (Dec. 22, 2004) 5 pages.

Atlas European Standard Transducers; http://www.panametrics-ndt.com/ndt/ndt_transducers/european_standard.html (Dec. 22, 2004) 3 pages.

*Combined Compression and Shear Wave Ultrasonic Measurements on Curing Adhesive*, R. J. Freemantle et al., Meas. Sci. Technol., (1998) pp. 1291-1302.

*A Technique for Accurate Shear Wave Velocity Measurements of Thin Epoxy Resin Samples Using Electromagnetic Acoustic Transducers (EMATs)*. S. Dixon et al., Measurement Science and Technology (2001) pp. 615-621.

U.S. Appl. No. 10/734,452, filed Dec. 12, 2003, In re: Bossi et al., entitled *Ultrasonic Inspection Device for Inspecting Components at Preset Angles*.

U.S. Patent Appl. No. 10/752,890, filed Jan. 7, 2004, In re: Bossi et al., entitled *Non-Destructive inspection Device for Inspecting Limited-Access Features of a Structure*.

U.S. Appl. No. 10/943,088, filed Sep. 16, 2004, In re: Georgeson et al., entitled *Magnetically Attracted Inspecting Apparatus and method Using a Ball Bearing*.

U.S. Appl. No. 10/943,135, filed Sep. 16, 2004; In re: Georgeson et al., entitled *Magnetically Attracted Inspecting Apparatus and Method Using a Fluid Bearing*.

U.S. Appl. No. 11/041,601, filed Jan. 24, 2005; In re: Safai et al., entitled *Real-Time X-Ray Scanner and Remote Crawler Apparatus and Method*.

U.S. Appl. No. 11/045,861, filed Jan. 28, 2005; In re: Georgeson et al., entitled *X-Ray Laminography Inspection System and Method*.

* cited by examiner

SIDE VIEW

FIG. 3A

FRONT VIEW

FIG. 3B

SIDE VIEW

FIG. 4A

FRONT VIEW

ANGLE BEAM SHEAR WAVE THROUGH-TRANSMISSION ULTRASONIC TESTING APPARATUS AND METHOD

CROSS-REFERENCE TO RELATED APPLICATIONS

The contents of U.S. Pat. No. 6,722,202 and application Ser. No. 10/734,452, entitled "Ultrasonic Inspection Device for Inspecting Components at Preset Angles," filed Dec. 12, 2003; application Ser. No. 10/752,890, entitled "Non-Destructive Inspection Device for Inspection Limited-Access Features of a Structure," filed Jan. 7, 2004; application Ser. No. 10/943,088, entitled "Magnetically Attracted Inspecting Apparatus and Method Using a Ball Bearing," filed Sep. 16, 2004; application Ser. No. 10/943,135, entitled "Magnetically Attracted Inspecting Apparatus and Method Using a Fluid Bearing," filed Sep. 16, 2004; and application Ser. No. 11/045,861, entitled "X-Ray Laminography Inspection System and Method," filed Jan. 28, 2005, are incorporated by reference.

FIELD OF THE INVENTION

The present invention relates generally to an apparatus and method for inspecting a structure and, more particularly, to an apparatus and method for non-destructive angle beam shear wave through-transmission ultrasonic inspection of a structure.

BACKGROUND

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Among the structures that are routinely non-destructively tested are complex structures, such as castings and structures with internal walls and protruding boss elements, and composite structures, such as composite sandwich structures and other adhesive bonded panels and assemblies. These complex structures, and a shift toward lightweight composite and bonded materials, dictate that devices and processes are available to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, typical defects in composite sandwich structures, generally made of one or more layers of lightweight honeycomb or foam core material with composite or metal skins bonded to each side of the core, include disbonds which occur at the interfaces between the core and the skin or between the core and a buried septum.

Various types of sensors may be used to perform non-destructive inspection. One or more sensors may move over the portion of the structure to be examined, and receive data regarding the structure. For example, a pulse-echo (PE), through transmission (TT), or shear wave sensor may be used to obtain ultrasonic data, such as for thickness gauging, detection of laminar defects and porosity, and/or crack detection in the structure. Resonance, pulse echo or mechanical impedance sensors may be used to provide indications of voids or porosity, such as in adhesive bondlines of the structure. High resolution inspection of aircraft structure is commonly performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. Further, surface defects and discontinuities typically hide internal defects and discontinuities from traditional ultrasonic pulse echo methods. For example, a surface feature or attachment such as including a bolt or weld, repair-grind-out, or near-surface defect can mask interior defects and features. In through-transmission ultrasonic inspection, ultrasonic sensors such as transducers, or a transducer and a receiver sensor, are positioned facing the other but contacting opposite sides of the structure. An ultrasonic signal is transmitted by at least one transducer, propagated through the structure, and received by the other transducer. Data acquired by sensors is typically processed and then presented to a user via a display as a graph of amplitude of the received signal. To increase the rate at which the inspection of a structure is conducted, a scanning system may include arrays of inspection sensors, i.e., arrays of transmitters and detectors. As such, the inspection of the structure can proceed more rapidly and efficiently, thereby reducing the costs associated with the inspection. However, it has traditionally not been feasible to inspect internal defects of a structure using ultrasonic inspection because of surface defects and features.

Non-destructive inspection may be performed manually by technicians who typically move an appropriate sensor over the structure. Manual scanning requires a trained technician to move the sensor over all portions of the structure needing inspection.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For example, the Automated Ultrasonic Scanning System (AUSS®) system is a complex mechanical scanning system that employs through-transmission ultrasonic inspection. The AUSS system can also perform pulse echo inspections, and simultaneous dual frequency inspections. The AUSS system has robotically controlled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. Conventional automated scanning systems, such as the AUSS-X system, therefore require access to both sides or surfaces of a structure which, at least in some circumstances, will be problematic, if not impossible, particularly for very large or small structures. To maintain the transmitter and receiver in proper alignment and spacing with one another and with the structure undergoing inspection, the AUSS-X system has a complex positioning system that provides motion control in ten axes. Access to the structure to conduct inspection may be so limited that manual or automated inspection is not possible. Furthermore, scanning systems inspect limited areas up to a few meters square.

Many parts, however, incorporate features, such as internal wall and protruding boss elements, which prevent use of conventional scanning methods. Further, surface defects and discontinuities and structural elements of a part may limit the usefulness of conventional scanning methods.

SUMMARY OF THE INVENTION

The present invention provides an improved apparatus and method for inspecting a structure using angle beam shear wave through-transmission ultrasonic signals. Embodiments of the present invention combine shear wave ultrasonic inspection methods and technologies with magnetically coupled inspection probe technologies to provide angle beam shear wave inspection devices that are portable, can be used for various applications, and provide inspection results in real-time, including three-dimensional imaging of internal features of a structure. Such devices can be used for high resolution defect detection in structures of varying shapes and sizes, including structures such as bondlines, weldlines, and lap joints and structures including such obstructions as vertical stiffeners, webbings, and walls that prevent or limit access to regions of the structure. Embodiments of systems, apparatus, and methods of the present invention can be used for inspection of structures during manufacture or in-service. Further, embodiments of the present invention provide new inspection capabilities for non-destructive inspection of large and small structures, structures with limited-access features, and complex features of structures.

Systems, apparatus, and methods of the present invention typically use magnetically coupled probes including respective sensing elements that are disposed at offset positions on opposing surfaces of a structure. Additionally, systems, apparatus, and methods of the present invention are capable of operating in array modes, thereby increasing inspection speed and efficiency while reducing cost.

For continuous scanning applications using magnetically coupled probes, only one probe need be driven due to magnetic coupling between the probes, or magnetic coupling between one probe and a magnetic coupling device connected to the other probe by a support element. Thus, methods, systems, and apparatus of the present invention are advantageously adapted to inspect structures in which one surface of the structure is relatively inaccessible or structures which are exceptionally large and are advantageously capable of angle beam shear wave through-transmission ultrasonic inspection. Also, embodiments of methods, systems, and apparatus of the present invention permit the probes to contact and ride along the respective surfaces of the structure, thereby reducing or eliminating the necessary sophistication of a motion control system that is typically required by conventional scanning systems to maintain the probes in a predefined orientation and predefined positions with respect to each other and at a predefined spacing from the respective surface of a structure undergoing inspection. Manual inspection is also capable using magnetically coupled angle beam shear wave through-transmission ultrasonic inspection probes in accordance with an embodiment of the present invention. Permitting the probes to contact and ride along the respective surfaces of the structure also may maintain alignment between the probes and/or the angle beam shear wave ultrasonic sensors of the probes. The probes may use contact members to support the probes against the respective surfaces of the structure. Contact with the surface permits accurate position measurement of the inspection device during continuous scanning, such as keeping an optical or positional encoder in physical and/or visual contact with the surface of the structure under inspection. Contact with the surface also permits the probes to disperse a couplant between the surface of the structure and the angle beam shear wave ultrasonic sensors.

According to one aspect of the present invention, a method, apparatus, and system for non-destructive inspection of a structure using angle beam shear wave through-transmission ultrasonic signals may include two probes which are configured for traveling over separate surfaces of the structure. Each probe includes at least one magnetic coupling device for magnetically coupling the probe with the other such that the magnetic attraction holds the probes against opposing surfaces of the structure. The magnetic coupling between the probes causes movement of both probes when only one probe is driven. At least one of the probes may include a motor for moving the probe, adjusting the position of the probe on a support element, or adjusting the incident or extraction angle of a shear wave transducer. If a motor is used for moving a probe, the magnetically coupled probes can thereby move in a leader-follower format.

Each probe includes a shear wave transducer. The probes are configured such that the magnetic coupling between the probes holds the shear wave transducers at offset positions on opposing surfaces to permit angle beam shear wave through-transmission ultrasonic inspection of the structure. The magnetic coupling devices of the probes may be magnets configured to provide magnetic attraction between the probes or a magnet and a ferromagnetic material to provide the magnetic attraction between the probes.

One probe may include an insertion transducer mount for supporting the shear wave transducer of that probe; the other probe may include an extraction transducer mount for supporting the shear wave transducer of that probe. Insertion and extraction transducer mounts and the shear wave transducers may be exchangeable so they can be removed and replaced with transducers and transducer mounts with different insertion and extraction angles for the angle beam shear wave through-transmission ultrasonic inspection. In addition, or alternatively, insertion and extraction transducer mounts may be capable of supporting the shear wave transducers at more than one insertion and extraction angle, such as being adjustable or having multiple fixed positions for supporting shear wave transducers. The insertion and extraction transducer mounts may be capable of supporting the shear wave transducers at angles to opposing surfaces of a structure, where the angles are between a first critical angle for the material of the structure defined such that shear waves are generated into the structure but longitudinal waves are mode converted into surface waves and a second critical angle for the material of the structure defined such that both shear waves and longitudinal waves are mode converted into surface waves. Typical insertion and extraction angles may be approximately 45°.

One of the probes may include a display communicably coupled to the receiving shear wave transducer for presenting inspection images captured by the shear wave transducer. By including a display a technician can analyze the inspection data and/or positional information in real-time during the inspection operation. A display may be co-located with a probe of an apparatus as in FIG. 1 or communicably connected to a receiving angle beam shear wave ultrasonic transducer and remotely located. The probe may include a wireless receiver for communicably coupling the display to the receiving shear wave transducer. The probe may further include a processing element for generating an image for presenting on the display. Another probe may include a wireless transmitter communicably coupled to the receiving shear wave transducer for transmitting inspection data captured by the shear wave transducer. The probe may also include a processing element for generating inspection data from the signals from the receiving shear wave transducer. At least one of the probes may also include a visual inspection sensor for providing position or optical information related to the location of one of the probes or shear wave transducer thereof.

According to another aspect of the present invention, a method, apparatus, and system may include transmitting and receiving ultrasonic signals with shear wave transducers that are magnetically coupled at offset positions on opposing surfaces of a structure, and a processing element capable of identifying a defect in the structure from the relationship of the transmitted and received ultrasonic signals of the shear wave transducers. A support element may be included for positioning one shear wave transducer in an offset position from the other shear wave transducer. An insertion or extraction transducer mount may be included to support a respective shear wave transducer and connect the shear wave transducer to the support element. The support element may be configured for adjusting the position of a shear wave transducer for changing the offset positions of the shear wave transducers, thereby changing the angle for inspecting a structure.

According to yet another aspect of the present invention, a method, apparatus, and system may generate a three-dimensional image representation of at least a portion of the structure under inspection, possibly including three-dimensional image representations of at least a portion of a feature of or a defect in the structure. A processing element may be used to analyze data for inspecting the structure. For example, as described above, a processing element may generate inspection data from the signals from the receiving shear wave transducer. A processing element may further analyze inspection data to identify a defect in the structure. For example, a processing element may identify a defect in a structure based on a relationship of the received portion of the transmitted ultrasonic signal and a predetermined threshold, such as a predetermined threshold based on the transmitted ultrasonic signal or based on an estimated expected received signal. A processing element may further be capable of generating a three-dimensional image representation of at least a portion of the structure and/or a feature of or a defect in the structure. For example, one or more received angle beam shear wave ultrasonic signals may be used to generate a three-dimensional image representation.

According to yet another aspect of the present invention, a method, apparatus, and system may generate a three-dimensional image representation using pulse-echo ultrasonic inspection data in addition to angle beam shear wave through-transmission ultrasonic signal inspection data. Pulse-echo ultrasonic inspection data may be used to supplement the angle beam shear wave through-transmission ultrasonic signal inspection data. Although pulse-echo ultrasonic inspection has limitations as a complete inspection technique, pulse-echo ultrasonic inspection, such as using a far-side, receiving transducer, may be used to improve three-dimensional defect resolution. For example, distance data can be determined directly from a pulse-echo signal time-of-flight, thereby improving the depth measurement for a three-dimensional image representation. Similarly, variations in the amplitude of a pulse-echo inspection signal can provide information for reconstructing a defect. Pulse-echo inspection signal amplitude can be affected by variations in surface orientations of a defect. Facets of a defect that are more perpendicular to a pulse-echo signal will reflect a return signal with high amplitude. Facets of a defect that are more parallel to a pulse-echo signal will reflect a return signal with low amplitude. Thus, a method, apparatus, and system of the present invention may use pulse-echo distance and/or amplitude data to improve three-dimensional image generation.

DETAILED DESCRIPTION

The present invention will be described more fully with reference to the accompanying drawings. Some, but not all, embodiments of the invention are shown. The invention may be embodied in many different forms and should not be construed as limited to the described embodiments. Like numbers and variables refer to like elements and parameters throughout the drawings.

When angle beam shear wave transducers have typically been used for non-destructive inspection, a shear wave transducer bounces an ultrasonic signal at an angle off the back and/or end of a structure such that the signal is repeatedly reflected, and the same transducer catches the multiple-reflected signal or a different transducer catches the signal on the same side of the structure as the transmitting transducer. This method may be referred to as angle beam shear wave pitch-catch. The use of angle beam shear waves with multiple reflections may permit inspection of the inside of a structure behind a surface defect or feature, but make the signal too complicated to fully characterize internal defects and features, and the significant path length of multiple reflections reduces defect sensitivity and resolution.

By comparison, the present invention uses shear wave transducers on opposing surfaces of the structure that allows for single pass, zero reflection angle beam shear wave ultrasonic inspection, which permits inspection of the inside of the structure beneath surface defects and features and allows for three-dimensional imaging of these areas and defects and features in these regions. Three-dimensional imaging of the inside of the structure is simplified by the single pass, zero reflection angle beam shear wave ultrasonic inspection, but also by one-sided control of magnetically coupled shear wave transducers. By moving transducers to various locations and/or making multiple passes with an inspection device, a processing device can produce a three-dimensional image of the interior of the structure. A computer or other processing device may construct the three-dimensional image from measurements of ultrasonic attenuations similar to x-ray computer tomography. The signal amplitude, normalized to the transmitted path length, can be measured and saved for each projection. A three-dimensional image can be generated by collecting a volume of projections such as moving the magnetically coupled shear wave transducer pairing in a grid pattern, rotation, or combination of motion and rotation. The exact positions of the transducers are recorded for each protection, such as using a positional encoder, to permit the processing device to interpret the signal amplitude of the projection through a particular path of the structure. Using the signal and position data, the processing device can generate a three-dimensional image. Detail and accuracy can be improved by increasing the number of projections and/or varying the vector directions for the projections. The resulting three-dimensional image may be presented on a display for a technician, and associated software may permit manipulation and/or analysis of the inspection data and resulting three-dimensional image.

Figure 1:
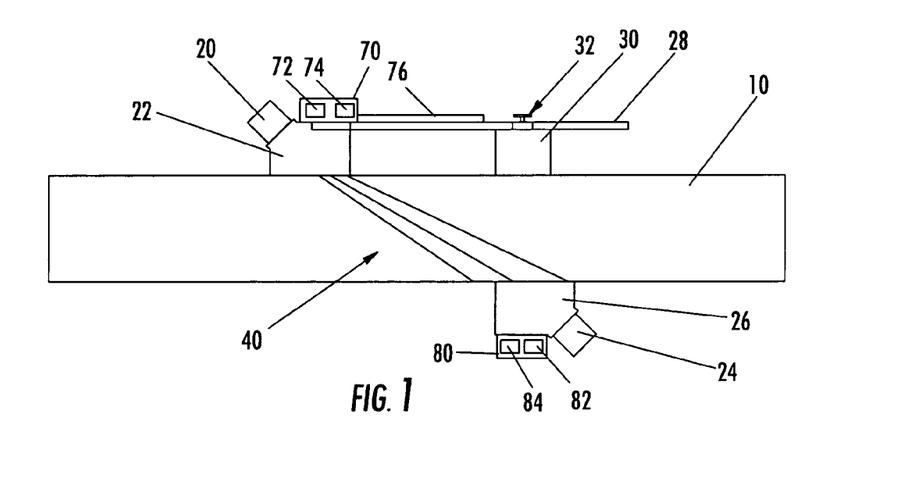
FIG. 1 is a block diagram of an embodiment of an angle beam shear wave through-transmission ultrasonic inspection apparatus of the present invention.
Figure 2:
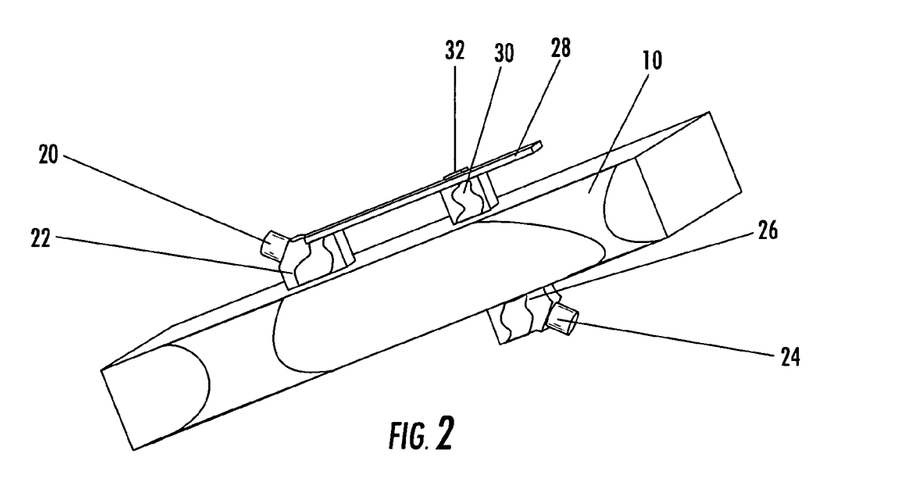
FIG. 2 is a schematic diagram of another embodiment of an angle beam shear wave through-transmission ultrasonic inspection apparatus.

Angle beam shear wave ultrasonic inspection devices can inspect a variety of structures formed of various materials. For inspection devices which transmit magnetic fields through the structure, however, the structure is preferably non-magnetic, that is, the structure preferably has no magnetic permeability. Structures that may be inspected with an embodiment of an inspection device of the present invention may include, but are not limited to, composites such as carbon fiber or graphite reinforced epoxy (Gr/Ep), non-ferromagnetic metals (e.g. aluminum alloy, titanium alloy, or aluminum or titanium hybrid laminates such as GLARE or Ti/Gr), and polymers. While a portion of a relatively simple structure is depicted in FIGS. 1 and 2, a structure being inspected may be any myriad of shapes and/or sizes and used in a variety of applications, including aircraft, marine vehicles, automobiles, spacecraft and the like, as well as buildings. Moreover, the structure may be inspected prior to assembly or following assembly, as desired.

The present invention allows inspection beneath the surface of the structure, including beneath surface defects and discontinuities which typically hide deeper defects and discontinuities from traditional ultrasonic normal incidence and pulse echo methods.

Referring to FIGS. 1 and 2, embodiments of angle beam shear wave through-transmission ultrasonic inspection systems, apparatus, or methods may operate using a pair of probes positioned on opposing surfaces of a structure. Corresponding transducers 20, 24 of the probes are oriented with respect to each other in offset positions, i.e., the transducers 20, 24 are not aligned directly across from each other through the structure 10, but are separated to permit inspection of the structure 10 using angle beam shear wave ultrasonic signals 40. Separating the transducers 20, 24 allows inspection beneath surface features that might otherwise block or interfere with inspection of the structure using inspection signals perpendicular to the surface of the structure.

The probes incorporate transducer mounts 22, 26 to support and orient the transducers 20, 24. In addition to supporting and orienting the transducers, the transducer mounts also transfer the ultrasonic signals from the transducers into the structure. An angle beam shear wave transducer uses a transducer mount, typically made from a sound absorbent material such as Lucite, with the principles of refraction and mode conversion to translate a longitudinal ultrasonic signal through the transducer mount to the intersection with the surface of the structure where the longitudinal ultrasonic signal is refracted and mode converted into a shear wave that can translate through the structure at an angle. A transducer mount will support and orient a transducer at an angle selected or adjusted to be between two critical angles. A first critical angle occurs where shear waves are generated into the structure, but longitudinal waves are mode converted into surface waves. A second critical angle occurs where both shear waves and longitudinal waves are mode converted into surface waves. A typical insertion angle for materials is approximately 45°, but optimized insertion and extraction angles can be determined independently for the angle beam shear wave ultrasonic inspection of each structure material. Particular first and second critical angles are dependent upon the material of the structure. Snell's Law can be used to correlate the velocity of waves through the materials using the equation of $$\sin\frac{U_i}{c_i} = \sin\frac{U_{rl}}{c_{rl}} = \sin\frac{U_{rs}}{c_{rs}} \qquad \text{(Eq. 1)}$$

where $U_i$=incident angle of the transducer mount, $U_{rl}$=angle of refracted longitudinal wave, $U_{rs}$=angle of refracted shear wave, $c_i$=longitudinal velocity of incident material (transducer mount), $c_{rl}$=longitudinal sound velocity of structure material, and $c_{rs}$=shear wave velocity of structure material. The angle of incidence or extraction for a transducer mount may be fixed, or a transducer mount may be configured to permit adjustment of the angle beam shear wave transducer. For example, a transducer mount may incorporate a plurality of fixed-angle positions for supporting an angle beam shear wave transducer. Alternatively, a transducer mount may include a rotatable support mechanism to allow adjustment of a transducer to any desired angle permitted by the configuration of the rotatable support mechanism. For example, an electronically-controlled motor may be used to adjust the incident or extraction angle of an angle beam shear wave transducer in a transducer mount with a rotatable support mechanism to any angle between first and second critical angles for a particular test material. Alternatively, a transducer mount may be configured for replacement in a probe, such as removing a 40° transducer mount and replacing it with a 45° transducer mount in a probe that is configured for exchanging different transducer mounts.

Depending upon the application and inspection environment, a couplant, such as an ultrasonic gel or water, may be used between the transducer mount and the surface of the structure to provide a good stress wave path from the transducer mount into the structure, and possibly as a lubricant for moving the probe over the surface of the structure.

The probes also provide for magnetic coupling to maintain offset positions of the angle beam shear wave ultrasonic transducers 20, 24. In FIGS. 1 and 2, magnetic coupling devices couple the transducer holder 26 of the lower probe to a support element 28, 30 connected to the transducer mount 22 of the upper probe. For example, the magnetic attraction of the magnetic coupling devices holds the transducer mount 26 of the lower probe in an offset position from the transducer mount 22 of the upper probe to permit use of angle beam shear wave through-transmission ultrasonic signals for inspection of the structure 10. Magnetic coupling may be provided by a magnet, such as a permanent magnet or an electromagnet, or a ferromagnetic material. Magnetic coupling may be adjusted by changing the size and/or strength of a magnetic coupling device. For example, to decrease the effects of friction, electromagnetic strength may be decreased, but to increase the holding support of the magnetic coupling, electromagnetic strength may be increased. For example, for inspection applications where the structure is relatively thin and the magnetic attraction is strong enough to make moving the inspection apparatus difficult, the magnetic attraction may be reduced, such as decreasing the strength of an electromagnet or using non-ferromagnetic material spacers to separate the magnetic coupling devices of opposing probes. Example configurations of magnetic coupling devices are described with respect to FIGS. 3A, 3B, 4A, 4B, 5A, and 5B.

A support element may be configured to orient angle beam shear wave transducers at fixed offset positions. Alternatively, as shown with respect to the support element 28, 30 of FIG. 1, a support element may be adjustable in that a portion 30 of the support element may be formed of a magnetic coupling device that is attached to the other portion 28 of the support element using an adjustment mechanism 32 with a releasable pin or screw device. The portion 28 of the support element connects the magnetic coupling device to the angle beam shear wave transducer 20. A support element may be manually adjustable using a mechanical adjustment mechanism, such as a mechanical slide with a releasable pin or screw device that allows an operator to set the distance between angle beam shear wave transducers. Alternatively, a support element may be electronically adjustable, such as using an electronically-controlled smart stepper motor. Because the probes are coupled by corresponding magnetic coupling devices, the probes can be positioned in an offset position where the magnetic coupling device of at least one of the probes is laterally separated from the angle beam shear wave ultrasonic transducer of that probe, such as in the configuration of FIGS. 1 and 2 where the magnetic coupling element of the portion 30 of the support element is separated from the angle beam shear wave ultrasonic transducer 20 of the probe, but magnetically coupled to the probe on the opposing surface of the structure, where that probe includes a magnetic coupling element proximate the angle beam shear wave ultrasonic transducer 24. The lateral separation between the magnetic coupling device and the angle beam shear wave ultrasonic transducer 20 of the top probe provides offset positions for both of the corresponding angle beam shear wave ultrasonic transducers 20, 24.

The probes may also include or otherwise be associated with a computing device 70, 80 including a processing element 72, 82, a wireless transmitter 84, and/or a wireless receiver 74. A computing device 70, 80 may further include elements, such as memory and storage devices, that function with a processing element, wireless transmitter, or wireless receiver. A display 76 may be connected to a processing element 72 for presenting real-time inspection data, such as three-dimensional image representations of an inspection. A processing element 72, 82 may operate to control a motor that moves a probe, adjusts the position of a magnetic coupling device on a support element, or adjusts the angle of incidence or extraction of an angle beam shear wave transducer in a transducer mount.

Embodiments of the present invention may be capable of wireless operation, such as wireless transmission of inspection data from received angle beam shear wave and pulse-echo ultrasonic signals. Accordingly, at least one of the magnetically coupled probes, typically the probe supporting the receiving angle beam shear wave ultrasonic transducer, can be used wirelessly without having to feed wires into the structure for transmission of the digital images, and possibly also for powering the device. In many situations, the wireless operation, and cordless capability, of an inspection probe may be advantageous, such as in a situation where the magnetically coupled probe and a receiving angle beam shear wave ultrasonic transducer are used in limited access areas or near backside structures such as weldlines and boss features. To provide a completely wireless inspection probe, battery power may be used for any type of equipment which requires power, such as operation of the angle beam shear wave ultrasonic transducers, a wireless transmitter, any motors used to control the probes or adjust configurations of the probes, and any encoders used to record position and/or orientation data about the probes.

To perform inspection of the structure, the probes are moved over the opposing surfaces of the structure. A motor, such as an electronically-controlled smart stepper motor, may be used to control the movement of an inspection apparatus or system over opposing surfaces of a structure. The probes may use contact members to support the probes against the respective surfaces of the structure. A contact member may be any variety of devices capable of supporting a probe against a surface of a part, including, but not limited to, a wheel, a ball bearing, a fluid bearing, a skid, a tread, or a combination of the fore-mentioned contact members. Contact with the surface permits accurate position measurement of the inspection device during continuous scanning, such as keeping an optical or positional encoder in physical and/or visual contact with the surface of the structure under inspection. Various types of visual inspection sensors may be used with the present invention, such as a positional encoder, an optical encoder, a linear encoder, a camera, a directional sensor, or a wheel encoder. Contact with the surface also permits the probes to disperse a couplant between the surface of the structure and the angle beam shear wave ultrasonic transducers and transducer mounts.

As the probes are moved, inspection data is collected for the various positions of the probes. Through-transmission ultrasonic inspection data is captured from the angle beam shear wave transducers. The inspection data is processed for analysis of the structure. For example, a processing element can inspect the structure based on a relationship of a predetermined threshold to that portion of the ultrasonic signal that was originally generated by a transmitting angle beam ultrasonic transducer that is received by a receiving angle beam shear wave transducer. A transmitting angle beam ultrasonic transducer generates an ultrasonic signal with a particular signal strength or amplitude. Only a portion of the ultrasonic signal will be transmitted into the structure as an angle beam shear wave. However, the receiving angle beam ultrasonic transducer receives only a portion of the ultrasonic signal transmitted into the structure as an angle beam shear wave. A processing element can compare the relationship of the received portion of the ultrasonic signal to a predetermined threshold based on any of the intervening levels, such as the ultrasonic signal originally generated and transmitted by the transmitting angle beam transducer or the portion of the ultrasonic signal transmitted into the structure. Comparison of signal strengths can be used to identify features and defects in the structure. The path length of the angle beam shear wave ultrasonic signal is typically taken into consideration to normalize the received signal amplitude of different through-transmission ultrasonic inspections. Because of different part thicknesses, offset positions, and angles of inspection, different inspection applications will necessarily have different results based at least in part on the different path lengths of a zero-reflection, single-pass through-transmission inspection technique. Accordingly, the path length can be used to normalize inspection data.

In operation, an angle beam shear wave through-transmission ultrasonic inspection apparatus, system, or method of an embodiment of the present invention may operate using a pulser card that sends an electrical impulse to a transmitting angle beam shear wave ultrasonic transducer. The transmitting transducer generates an ultrasonic pulse that travels through an insertion transducer mount, makes a mode conversion at the intersection with the structure from a longitudinal wave to a shear wave, travels through the structure, makes a mode conversion at the intersection with an extraction transducer mount from a shear wave to a longitudinal wave that is received by a receiving angle beam shear wave transducer. The receiving transducer converts the longitudinal stress wave into an electrical pulse which travels to a receiver board for analysis using a processing element. The apparatus, system, or method may be arranged by an operator by determining the proper offset position for the transducers from the structure thickness and the angle of the shear wave through the structure.

By way of example, an embodiment of the present invention may be used for collection of inspection data around a weld line. Probes with transducer mounts and transducers are positioned on opposing surfaces of a structure with the transducers supported in offset positions on either side of the weld line. The angle beam shear wave ultrasonic signal inspection occurs beneath the surface to permit the inspection of weld line. If the probes are magnetically coupled, moving one probe toward the weld line moves the other probe away from the weld line. The inspection data will move vertically over the weld line. Moving magnetically coupled probes parallel to the weld line will provide lateral inspection data of the weld line. Complete inspection of the weld line can be performed through inspection at and along a plurality of positions with respect to the weld line. A defect, such as a crack, in the weld line will reduce or eliminate the transmission of the shear wave in the direction of the receiving transducer, and will be monitored as a loss in signal amplitude at that three-dimensional position. In such a manner, an embodiment of the present invention can be used to develop a three-dimensional image representation of actual defects, not merely a computed model of expected defect locations. For example, an embodiment of the present invention can determine exact positioning of a defect in three-dimensions with respect to a three-dimensional representation of the structure, rather than just approximating a depth location for a defect perceived in a structure using two-dimensional scanning or three-dimensional scanning without the capability of inspecting beneath surface defects and features.

A processing element may be capable of generating a three-dimensional image representation of at least a portion of the structure from two or more angle beam shear wave ultrasonic signals. Typically, a plurality of angle beam shear wave ultrasonic signals are used to generate a three-dimensional image representation. For example, the inspection apparatus or system can be moved to various locations on the structure, such as by making multiple linear passes or following a grid pattern, to obtain inspection data from a plurality of angle beam shear wave ultrasonic signals representing a three-dimensional volume of the structure. The inspection data is collected, such as stored in memory and/or storage devices of a computer device, and analyzed by a processing element to generate a three-dimensional image representation of the inspection. The exact position of the transducers are recorded during inspection, each time an ultrasonic signal amplitude is measured, to correlate the inspection data and the generation of a representative three-dimensional image of the structure, and any defects or features thereof. For example, position encoders may be used to record the three-dimensional coordinate data for the positions and orientations of the transducers during inspection. Alternatively, a computer controlling the movement of the probes and operation of the transducers can record the positions of the probes and transducers throughout an inspection.

In addition to angle beam shear wave ultrasonic inspection data, pulse-echo ultrasonic inspection data may be captured from one of the angle beam shear wave transducers or a separate pulse-echo ultrasonic transducer. For example, if an inspection system has a second active channel available, another transducer can be used in a pulse-echo mode or the far-side angle beam shear wave transducer can be used in pulse-echo mode in addition to the through-transmission mode. Although pulse-echo ultrasonic inspection has limitations as a complete inspection technique, pulse-echo ultrasonic inspection, such as using the far-side receiving angle beam shear wave transducer, may be used to supplement and thereby improve three-dimensional image resolution and generation using angle beam shear wave through-transmission ultrasonic inspection data. For example, distance data can be determined directly from a pulse-echo signal time-of-flight, thereby improving the depth measurement for a three-dimensional image representation. Because the ultrasonic shear wave speed in the material under test may be known or may be determined experimentally, the time-of-flight of the pulse-echo ultrasonic signal inspection provides the distance to the defect equal to the speed of the ultrasonic signal in the test material multiplied by half the time-of-flight. Although defect and feature depths can be determined using angle beam shear wave through-transmission ultrasonic signals for inspection, pulse-echo inspection provides an immediate measurement from a single angle. Improved depth measurement allows better defect characterization with less data. In addition, variations in the amplitude of a pulse-echo inspection signal can provide information for reconstructing the surface orientations of a defect in or feature of a structure. For example, pulse-echo inspection signal amplitude can be affected by variations in surface orientations of a defect, such as how facets of a defect that are more perpendicular to a pulse-echo signal will reflect a return signal with high amplitude and facets of a defect that are more parallel to a pulse-echo signal will reflect a return signal with low amplitude. Thus, the pulse-echo inspection amplitude data can be used for accurately locating defects and characterizing the shape and orientation of a defect based on the amplitude a return signal from the defect. Accordingly, a method, apparatus, and system of the present invention may use either or both pulse-echo distance and/or amplitude data to improve three-dimensional image generation.

Figure 3A:
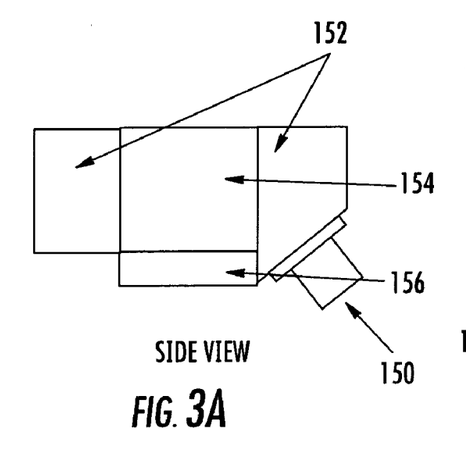
FIGS. 3A and 3B are schematic diagrams of a probe for yet another embodiment of an angle beam shear wave through-transmission ultrasonic inspection apparatus.
Figure 3B:
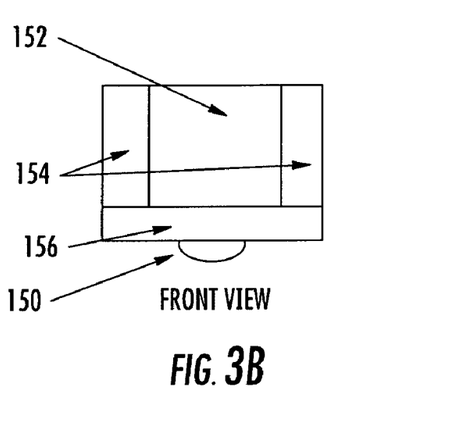

Referring to FIGS. 3A, 3B, 4A, 4B, 5A, and 5B, probes for other embodiments of angle beam shear wave through-transmission ultrasonic inspection apparatus are shown. The probe of FIGS. 3A and 3B is one design for a magnetically coupled far-side probe receiving angle beam shear wave ultrasonic signals. The probe includes an angle beam shear wave ultrasonic transducer 150 supported by an extraction transducer mount 152. The transducer mount 152 may be formed from a sound absorbent material, such as Lucite. Magnets 154 may be positioned on the sides of the transducer mount 152. A steel plate 156 may be used to hold the transducer mount 152 within the magnetic coupling provided by the magnets 154. A probe such as shown in FIGS. 3A and 3B may be magnetically coupled to a magnetic coupling device attached to a support element at an offset position from a second probe.

Figure 4A:
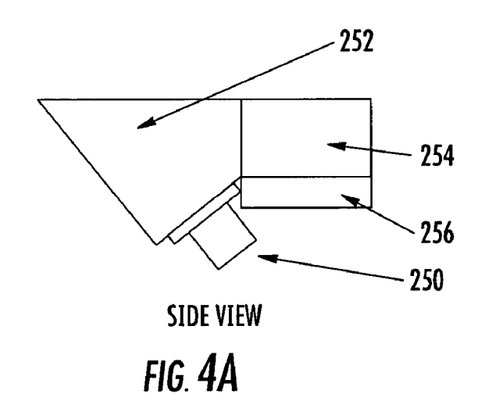
FIGS. 4A and 4B are schematic diagrams of another probe for yet another embodiment of an angle beam shear wave through-transmission ultrasonic inspection apparatus.
Figure 4B:
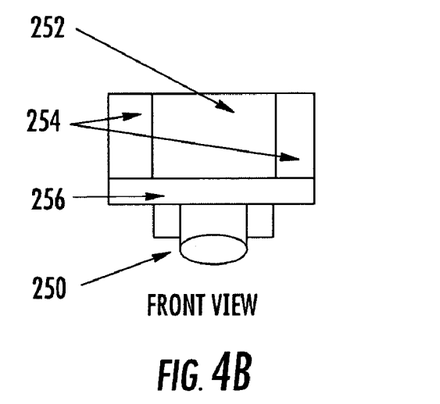

The probe of FIGS. 4A and 4B is one design for a magnetically coupled far-side probe receiving angle beam shear wave ultrasonic signals near a boss, wall, or ridged weld. When inspecting near a boss, wall, ridged weld, or similar feature of the structure, the feature may prevent the transducer mount 252 from sitting directly over the inspection area. Thus, the position of the angle beam shear wave ultrasonic transducer 250 supported by the transducer mount 252 can be relocated to the front of the transducer mount 252 such that ultrasonic signals are received, and/or transmitted, at the front of the transducer mount 252 where the transducer 250 is located. The magnetic coupling device, e.g., magnets 254 on the sides of the transducer mount and a steel plate 256 holding the transducer mount 252 to the magnets 254, may be positioned at the opposite end of the transducer mount 254.

Figure 5A:
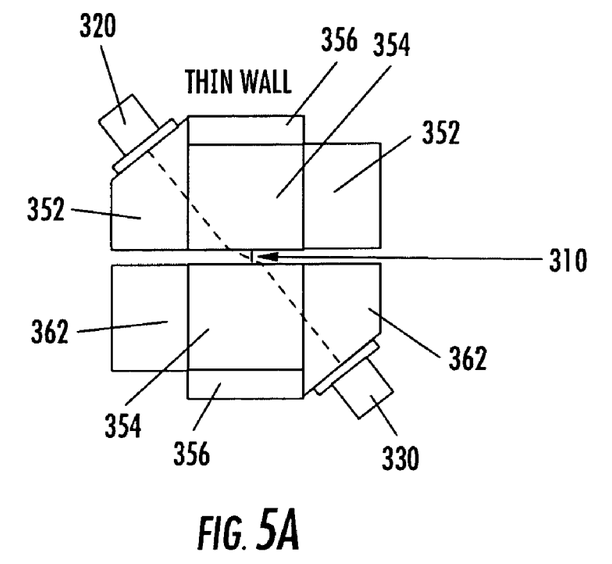
FIGS. 5A and 5B are schematic diagrams of probes for yet another embodiment of an angle beam shear wave through-transmission ultrasonic inspection apparatus.
Figure 5B:
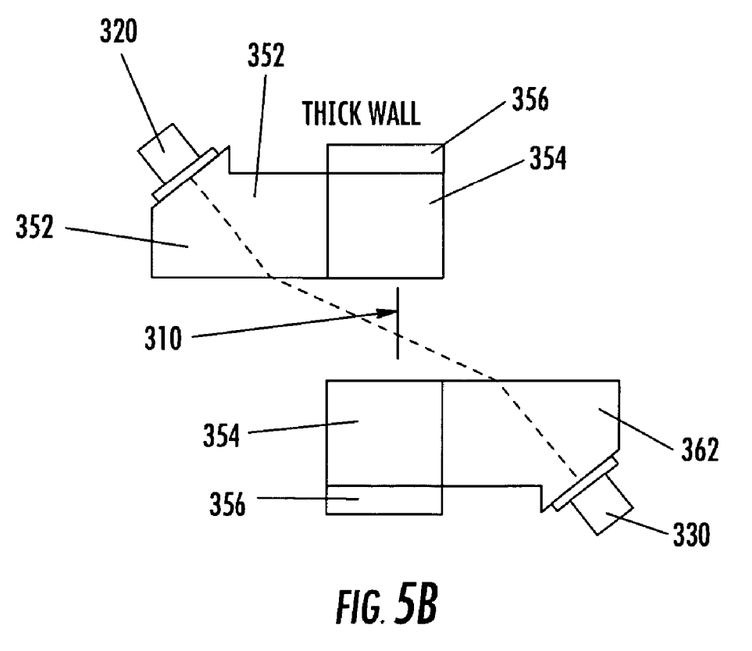

Rather than using a separate support element to define the offset position between the angle beam shear wave ultrasonic transducers, one or both of the probes may be designed to be capable of positioning the transducers at offset positions. Further, one or both of the probes may be designed to be capable of adjusting the offset positions of the transducers, such as to accommodate inspection of structures of different thicknesses or structures of different materials requiring different distances between the transducers. The probes in FIGS. 5A and 5B are capable of defining offset positions between the angle beam shear wave ultrasonic transducers 320, 330 and are further capable of being adjusted to accommodate inspection of structures of different thicknesses or structures of different materials. The magnetic coupling devices 354, 356 on the probes are capable of magnetically coupling the transducer mounts 352, 362 of the probes at different locations. For example, the magnetic coupling devices 354, 356 can slide along the length of the transducer mounts 352, 362 to change the positions of the angle beam shear wave transducers 320, 330 supported by the transducer mount 352, 362 when the magnetic coupling devices 354, 356 support the probes on opposing sides of a structure at offset positions. Holes, such as threaded holes, in a transducer mount may be used to accommodate a pin or a bolt to hold a magnetic coupling device at a fixed position on the transducer mount. The structure thickness and the angle the shear wave travels through the structure will determine the appropriate physical distance between the angle beam shear wave ultrasonic transducers. For example, the more acute angle of the transmission of the signal through the structure, the further apart transducers will be positioned. Similarly, the thicker the part, the further apart transducers will be positioned, as shown in FIG. 5B in comparison to FIG. 5A. The offset can be has as wide as permitted by the most acute insertion and extraction angles (first critical angle described above) and the thickness of the structure or as narrow as permitted by the least acute insertion and extraction angles (second critical angle described above) and the thickness of the structure. The thicker the structure, the wider the offset. The more acute the insertion and extraction angle, the wider the offset. Also, the overall ultrasonic signal strength, shear wave transmission into the structure, and shear wave transmissivity through the material of the structure will limit the total path length permitted for a particular application.

In addition to using magnetically coupled probes with angle beam shear wave transducers and/or support elements to define offset positions for the transducers, a three-dimensional reconstruction of a structure can be formed using other methods that provide known positioning of angle beam shear wave transducers on opposing surfaces of a structure, such as using two motion-controlled robotic arms, one on each side of the structure, thereby eliminating the need for magnetic coupling. For example, embodiments of the present invention may be scaled and adapted to be driven by an automated system, such as an AUSS system. A pair of robotic arms, one on each side of a structure, can be used to position and move the probes. However, using magnetic coupling to support and position the probes on opposing surfaces of the structure permits single-sided control of both probes, such as using a single motion-controlled robotic arm for manipulation and control of a front-side probe that is magnetically coupled to a back-side probe. For example, a yoke attachment may be attached to a magnetically coupled front-side probe and also connected to a scanning bridge of an automated system.

Improved methods, systems, and apparatus for inspecting a structure using angle beam shear wave through-transmission ultrasonic signals involves positioning transducers at offset positions on opposing sides of the structure and permits inspection of the inside of the structure beneath surface defects and features. Magnetic coupling can be used for supporting a pair of leader-follower probes and defining offset positions between angle beam shear wave transducers carried by the probes. Inspection data can be collected for supporting real-time generation of three-dimensional image representations of the structure and of internal defects and features of the structure. Image generation and resolution using inspection data from angle beam shear wave ultrasonic signals can be supplemented using pulse-echo ultrasonic inspection data.

The invention should not be limited to the specific disclosed embodiments. Specific terms are used in a generic and descriptive sense only and not for purposes of limitation.

That which is claimed:

1. A non-destructive inspection apparatus for inspecting a structure, comprising:
   a first probe configured for traveling over a first surface of the structure under inspection, the first probe comprising:
   at least one magnetic coupling device; and
   at least one shear wave transducer capable of transmitting ultrasonic signals into the first surface of the structure for inspecting the structure as the first probe is moved over the first surface of the structure, wherein the ultrasonic signals are transmitted into the structure as a shear wave at an angle to the first surface; and a second probe configured for traveling over a second surface of the structure for through transmission inspection, the second probe comprising:
at least one magnetic coupling device for magnetically coupling the second probe with the first probe, wherein the magnetic attraction of the magnetic coupling holds the first and second probes against the first and second surfaces of the structure, respectively, and wherein the first and second probes cooperate by the magnetic coupling to move in a leader-follower format; and
at least one shear wave transducer capable of receiving ultrasonic signals transmitted as a shear wave at an angle through the structure from the shear wave transducer of the first probe, wherein the first and second probes are further configured to hold the shear wave transducers at offset positions to permit inspection using angle beam shear wave ultrasonic signals.

2. The apparatus of claim 1, wherein the first probe further comprises an insertion transducer mount for supporting the shear wave transducer capable of transmitting ultrasonic signals into the first surface, and wherein the second probe further comprises an extraction transducer mount for supporting the shear wave transducer capable of receiving ultrasonic signals transmitted through the structure.

3. The apparatus of claim 2, wherein the insertion and extraction transducer mounts are capable of supporting the shear wave transducers at more than one insertion or extraction angle.

4. The apparatus of claim 2, wherein the insertion and extraction transducer mounts are capable of supporting the shear wave transducers at angles to the first and second surfaces, where the angles are between a first critical angle for the material of the structure at which shear waves propagate into the structure but longitudinal waves are mode converted into surface waves and a second critical angle for the material of the structure at which both shear waves and longitudinal waves are mode converted into surface waves.

5. The apparatus of claim 2, where at least one probe is configured for dispersing a couplant between the shear wave transducer supported by the transducer mount thereof and the respective surface of the structure over which the probe is configured for traveling.

6. The apparatus of claim 1, wherein one probe further comprises a support element for positioning the magnetic coupling device of the probe at a predetermined distance from the shear wave transducer of the probe thereby magnetically coupling the other probe at an offset position to permit inspection using angle beam shear wave ultrasonic signals.

7. The apparatus of claim 6, wherein the support element is configured to permit adjustment of the positioning of the magnetic coupling device and the offset position of the other probe, thereby changing the angle for inspecting the structure using angle beam shear wave ultrasonic signals.

8. The apparatus of claim 1, wherein at least one probe further comprises a motor for moving the probe.

9. The apparatus of claim 1, further comprising a display communicably coupled to the shear wave transducer of the second probe for presenting inspection data of the ultrasonic signals transmitted through the structure and received by the shear wave transducer of the second probe.

10. The apparatus of claim 1, wherein at least one probe further comprises a visual inspection sensor selected from the group consisting of a positional encoder, an optical encoder, a linear encoder, a camera, a directional sensor, and a wheel encoder.

11. The apparatus of claim 1, wherein at least one probe further comprises at least one contact member for supporting the probe against the structure and contacting the respective surface of the structure over which the probe is configured for traveling, the contact member being selected from the group consisting of a wheel, a ball bearing, a fluid bearing, a skid, a tread, and a combination thereof.

12. A system for inspecting a structure, comprising:
a transmitting shear wave transducer disposed proximate a first surface of the structure, the transmitting shear wave transducer being capable of transmitting an angle beam shear wave ultrasonic signal into the structure at an angle to the first surface such that at least a transmitted portion of the ultrasonic signal passes through the structure at an angle and exits an opposing second side of the structure;
a receiving shear wave transducer disposed proximate the second surface of the structure at an offset position from the transmitting shear wave transducer, the receiving transducer being capable of receiving the transmitted portion of the angle beam shear wave ultrasonic signal;
at least one magnetic coupling device connected to each of the shear wave transducers for magnetically coupling the shear wave transducers at the offset position, wherein the magnetic attraction of the magnetic coupling holds the shear wave transducers proximate the first and second surfaces of the structure; and
a processing element capable of analyzing data for inspecting the structure based on a relationship of the transmitted portion of the ultrasonic signal received by the receiving transducer and a predetermined threshold.

13. The system of claim 12, further comprising a support element for positioning one of the shear wave transducers at a predetermined distance from the shear wave transducer of the other probe to establish the offset position, thereby disposing the shear wave transducers at the offset position to permit inspection of the structure using angle beam shear wave ultrasonic signals.

14. The system of claim 12, wherein the processing element is capable of identifying a defect in the structure based on a relationship of the transmitted portion of the ultrasonic signal received by the receiving transducer and a predetermined threshold.

15. The system of claim 14, wherein the processing element is capable of identifying a defect in the structure based on a relationship of the transmitted portion of the ultrasonic signal received by the receiving transducer and a predetermined threshold based on the ultrasonic signal transmitted by the transmitting transducer.

16. The system of claim 12, wherein the processing element is capable of representing a portion of the structure from one or more transmitted portions of angle beam shear wave ultrasonic signals received by the receiving shear wave transducer and transmitted to the processing element.

17. The system of claim 12, wherein the processing element is further capable of computing a three-dimensional representation of at least a portion of the structure from a plurality of transmitted portions of angle beam shear wave ultrasonic signals received by the receiving shear wave transducer and transmitted to the processing element.

18. The system of claim 17, wherein the processing element is further capable of computing a three-dimensional representation of at least a portion of a feature of the structure from a plurality of transmitted portions of angle beam shear wave ultrasonic signals received by the receiving shear wave transducer and transmitted to the processing element.

19. The system of claim 17, wherein the processing element is further capable of computing a three-dimensional representation of at least a portion of an identified defect in the structure from a plurality of transmitted portions of angle beam shear wave ultrasonic signals received by the receiving shear wave transducer and transmitted to the processing element.

20. A method for inspecting a structure, comprising the steps of:
supporting a first probe on a first surface of the structure and a second probe on an opposed second surface of the structure;
establishing magnetic attraction between the probes sufficient for holding the probes on the opposing surfaces of the structure;
moving one probe, wherein magnetic coupling between the probes causes the other probe to be moved along the opposing surface of the structure; and
transmitting an angle beam shear wave ultrasonic signal into and at an angle to the first surface of the structure from a first shear wave transducer carried by the first probe such that at least a transmitted portion of the ultrasonic signal passes through the structure at an angle and exits the opposing second surface of the structure and receiving the transmitted portion of the ultrasonic signal by a second shear wave transducer carried by the second probe as the proves move along the opposing surfaces of the structure,
wherein the first and second shear wave transducers are supported by the first and second probes such that one shear wave transducer is offset from the position of the other shear wave transducer to permit inspection of the structure using angle beam shear wave ultrasonic signals.

21. The method of claim 20, further comprising the step of identifying a defect in the structure based on a relationship of the transmitted portion of the ultrasonic signal received by the second shear wave transducer and a predetermined threshold.

22. The method of claim 20, further comprising the step of displaying inspection data of the ultrasonic signals transmitted through the structure and received by the second shear wave transducer.

23. The method of claim 20, further comprising the step of adjusting an insertion angle of the angle beam shear wave ultrasonic signal from the first shear wave transducer into the first surface and an extraction angle of the transmitted portion of the ultrasonic signal from the second surface to the second shear wave transducer.

24. The method of claim 20, further comprising the steps of:
sending a first electronic signal to the first shear wave transducer to effect the transmission of an angle beam shear wave ultrasonic signal for inspection of the structure;
converting the transmitted portion of the ultrasonic signal received by the second shear wave transducer into a second electronic signal; and
converting the second electronic signal into inspection data.

25. The method of claim 20, further comprising the steps of:
determining an insertion angle for the angle beam shear wave ultrasonic signal from the first shear wave transducer into the first surface of the structure; and
determining the offset positioning for the first and second shear wave transducers corresponding to the insertion angle.

26. A method for inspecting a structure, comprising the steps of:
supporting a first shear wave transducer proximate a first surface of the structure and a second shear wave transducer proximate an opposed second surface of the structure, wherein the first and second shear wave transducers are offset to permit inspection of the structure using angle beam shear wave ultrasonic signals;
moving the shear wave transducers in coordinated motion over the opposing surfaces of the structure while maintaining the offset positional relationship between the shear wave transducers;
transmitting an angle beam shear wave ultrasonic signal into the first surface of the structure from the first shear wave transducer such that at least a transmitted portion of the ultrasonic signal passes through the structure and exits the opposing second surface of the structure and receiving the transmitted portion of the ultrasonic signal by the second shear wave transducer as the proves move over the opposing surfaces of the structure; and
generating a three-dimensional image representation of at least portion of the inspected portion of the structure.

27. The method of claim 26, further comprising the step of identifying a defect in the structure based on a relationship of the transmitted portion of the ultrasonic signal received by the second shear wave transducer and a predetermined threshold.

28. The method of claim 27, further comprising the step of generating a three-dimensional image representation of at least a portion of the identified defect within the generated three-dimensional image representation of at least portion of the inspected portion of the structure.

29. The method of claim 26, further comprising the step of generating a three-dimensional image representation of at least a portion of a feature of the structure within the generated three-dimensional image representation of at least portion of the inspected portion of the structure.

30. The method of claim 26, further comprising the step of transmitting and receiving a pulse-echo ultrasonic signal into and from a surface of the structure.

31. The method of claim 30, wherein the step of generating a three-dimensional image representation of at least a portion of the inspected portion of the structure comprises supplementing the transmitted portion of the angle beam shear wave ultrasonic signal data with the received pulse-echo ultrasonic signal data.

32. The method of claim 31, wherein the step of supplementing the angle beam shear wave ultrasonic data with pulse-echo ultrasonic signal data comprises calculating distance data from the received pulse-echo ultrasonic signal data.

33. The method of claim 32, wherein the step of supplementing the angle beam shear wave ultrasonic data with pulse-echo ultrasonic signal data comprises calculating amplitude data from the received pulse-echo ultrasonic signal data.

34. The method of claim 31, wherein the step of supplementing the angle beam shear wave ultrasonic data with pulse-echo ultrasonic signal data comprises calculating amplitude data from the received pulse-echo ultrasonic signal data.

* * * * *